United States Patent [19]

Narisada et al.

[11] Patent Number: 5,200,533
[45] Date of Patent: Apr. 6, 1993

[54] INTERMEDIATES FOR PREPARATION OF 2,3-TRANS-1,4-BRIDGED CYCLOHEXANE SULFONAMIDE DERIVATIVES

[75] Inventors: Masayuki Narisada, Ibaraki; Mitsuaki Ohtani, Nara; Fumihiko Watanabe, Kitakatsuragi; Kyozo Kawata, Hirakata, all of Japan

[73] Assignee: Shionogi & Co., Ltd., Osaka, Japan

[21] Appl. No.: 851,291

[22] Filed: Mar. 12, 1992

Related U.S. Application Data

[60] Division of Ser. No. 711,562, May 30, 1991, Pat. No. 5,120,865, which is a continuation of Ser. No. 447,520, Dec. 7, 1989, abandoned.

[30] Foreign Application Priority Data

Dec. 14, 1988 [JP]  Japan ..................................... 315969

[51] Int. Cl.$^5$ .................. C07D 493/08; C07C 311/17
[52] U.S. Cl. ..................................... 549/463; 562/100
[58] Field of Search ........................ 549/463; 562/100

[56] References Cited

FOREIGN PATENT DOCUMENTS 0226346  6/1987  European Pat. Off. .
0312906  4/1989  European Pat. Off. .

OTHER PUBLICATIONS

Narisada et al., J. Med. Chem., 1988, 31, 1847–1854.
Gilbert, "Sulfonation and Related Reactions", Interscience Publishers, New York, New York (1965) pp. 157–160.

Primary Examiner—Bernard Dentz
Attorney, Agent, or Firm—Wenderoth, Lind & Ponack

[57] ABSTRACT

A process suitable for industrially preparing 2,3-trans-1,4-bridged cyclohexane sulfonamide derivatives, especially useful as an intermediate for the synthesis of a trans bicyclo[2,2,1] heptane carboxylic acid derivative, a clinically important thromboxane $A_2$ antagonist, comprising: allowing to react corresponding a cis/trans mixture of sulfonamide derivatives with an anionoid or water-soluble carbonyl reagent at pH 3–7 so that the trans isomer may form a water-soluble adduct with the anionoid or carbonyl reagent, separating the resulting adduct dissolved in an aqueous layer, and recovering the trans isomer by treating the adduct with a base or an acid. Also provided is an alkali metal hydrogen sulfite adduct of 2,3-trans 1,4-bridged cyclohexane sulfonamide derivative.

2 Claims, No Drawings

INTERMEDIATES FOR PREPARATION OF 2,3-TRANS-1,4-BRIDGED CYCLOHEXANE SULFONAMIDE DERIVATIVES

This application is a division of application Ser. No. 711,562, filed May 30, 1991 now U.S. Pat. No. 5,120,865 which application is a continuation of now abandoned application Ser. No. 447,520, filed Dec. 7, 1989.

This invention relates to a process for preparing 2,3-trans-1,4-bridged cyclohexane sulfonamide derivatives which are useful as an intermediate for the preparation of clinically important thromboxane $A_2$ antagonist. More particularly, it relates to a process for stereoselectively preparing the intermediate of the formula (I):

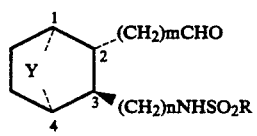

wherein R is phenyl or phenyl substituted with hydroxy, lower alkoxy, halogen or lower alkyl; Y is methylene, substituted methylene, ethylene, vinylene or oxygen; m is 0 or 1; n is 0, 1 or 2 with proviso that when m is 0, n is not 0, and when m is 1, n is not 2.

Thromboxane $A_2$, referred to as $TXA_2$ hereinafter, is a member of prostanoids which are biologically active substances and synthesized enzymatically from eicosapolyenoic acids, such as arachidonic acid in various animal tissues, for example, platelets, vascular walls, and the like. $TXA_2$ has been proved to exhibit many significant biological activities, such as aggultination of platelets and contraction of smooth muscle of various organs, e.g., bronchus, coronary artery, pulmonary artery, and the like, at a relatively low serum level of about $10^{-11}$-$10^{-12}$M. Because of these biological activities, $TXA_2$ has been considered to be one of the major causes of myocardial infarction, cerebral infarction, bronchial asthma, and thrombosis. Therefore, $TXA_2$ synthetase inhibitors which inhibit an enzyme responsible for the biosynthesis of $TXA_2$, or $TXA_2$ receptor antagonists which antagonize the binding of $TXA_2$ to its receptor, have been expected to be practically useful in the treatment and prevention of the above-mentioned diseases. However, the inhibitors are not suited for clinical use because inhibition of $TXA_2$ synthesis may result in accumulation of the precursor, i.e., prostaglandin $H_2$, which is believed to exhibit a biological activity similar to that of $TXA_2$. To the contrary, the receptor antagonists are thought to be useful for treating and preventing $TXA_2$-dependent diseases because they are not affected by the accumulated prostaglandin $H_2$.

In view of the above, the present inventors made extensive study and found that 1,4-bridged cyclohexane carboxylic acid derivatives, which are analogous compounds to $TXA_2$ or prostaglandin $H_2$, serve as an antagonist against $TXA_2$ and are chemically and biochemically stable [see, Japanese Patent Publication (Kokai) No. 139161/1988]. The inventors have continued the study in order to obtain more effective antagonists and found that trans isomers of said compounds are superior to cis isomers. The trans isomers are shown in the following general Formula (II):

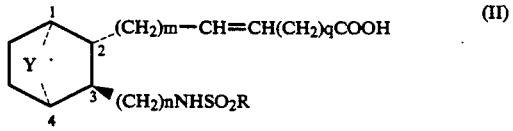

wherein R, Y, m, n have the same meanings as defined above, and q is 3 or 4.

The compounds above can be prepared according to the afore-mentioned Japanese patent publication, for example, the compound in which R is unsubstituted phenyl, Y is methylene, m is 1, n is 0, and q is 3, is prepared in the manner as described below starting from the compound of Formula 1:

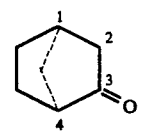

Specifically, an amine of Formula 2:

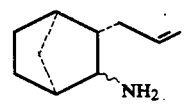

is first prepared from the above ketone 1 by introducing an allyl group at the 2-position, converting the carbonyl group at the 3-position into oxime, and reducing said oxime to an amino group giving a trans/cis mixture. After protection of the amino group, the amine 2 is oxidized at the allyl group giving an epoxide. The latter gives a trans/cis mixture of aldehydes of the following Formula 3 by oxidative cleavage:

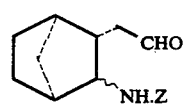

wherein Z is an amino-protecting group. The aldehyde 3 is then reacted with an ylide under reaction conditions of the Wittig Reaction. The resultant product is then esterified and deprotected with tri-fluoroacetic acid and anisole to give a free amine, which is then sulfonated with sulfonyl halide, such as phenylsulfonyl chloride, to form a trans/cis mixture of bicyclo[2,2,1]heptane carboxylic acid sulfonamide derivatives.

In order to obtain the trans isomer of the product, the mixture can be separated, for example, by chromatography on silica-gel. Alternatively, the intermediate aldehyde of Formula 3 can be separated in advance to obtain the trans isomer, which may be employed in the subsequent steps.

As can be seen from the above description, the previous procedures are too complicated to apply to an industrial mass-production of the desired trans carboxylic acid derivatives. In particular, the step for the separation of the trans isomer from the cis isomer effected by chromatography is time-consuming and also uneconomical. Therefore, it has been needed to establish a more simple and economical process for preparing the trans isomer of the afore-mentioned carboxylic acid derivatives.

The inventors have found (i) that a mixture of trans/cis compounds of Formula (I)':

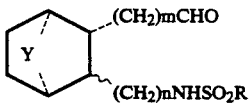

wherein R, Y, m and n have the same meanings as above, is easily produced by ozonolysis of a sulfonamide derivative of amine 2 at the allyl position, followed by treatment with triphenylphosphine, and (ii) that the trans isomer of the compound (I)' can form a reversible water soluble adduct (salt) upon treating with an anionoid reagent or a water-soluble carbonyl reagent, whereas the cis isomer can not, whereby both isomers can be separated from each other on the basis of the difference of their solubilities in an aqueous medium, and (iii) that as a result the trans isomer of the compound (I)' can be easily converted into the final trans carboxylic acid derivative. The present invention has been accomplished on the basis of those findings above.

Thus, this invention provides a process for preparing a 2,3-trans-1,4-bridged cyclohexane sulfonamide derivative of Formula (I), which comprises the steps:

(a) reacting a cis/trans mixture of 1,4-bridged cyclohexane sulfonamides of Formula (I)':

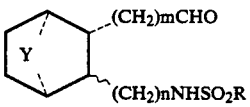

wherein R, Y, m, and n are as defined above, in a mixture of water and an organic solvent at pH 3-7 with an anionoid reagent or a water-soluble carbonyl reagent, which forms a water-soluble adduct only with the trans isomer of said sulfonamide (I)';

(b) separating an aqueous layer containing the water-soluble trans isomer in the form of the adduct from an organic layer containing the water-insoluble cis isomer; and (c) recovering the said trans isomer (I) by treating the aqueous layer obtained in step (b) with a base or an acid.

For the purpose of the present invention, as disclosed and claimed herein, the following terms are defined as below.

The term "lower alkyl" refers to a straight or branched saturated hydrocarbon radical having one to eight carbon atoms, including methyl, ethyl, n-propyl, isopropyl, butyl, isobutyl, sec-butyl, tert-butyl, pentyl, isopentyl, neopentyl, 1-methylbutyl, 1,2-dimethylbutyl, hexyl, heptyl, octyl, and the like.

The term "lower alkoxy" refers to $C_1$-$C_8$ alkoxy, including methoxy, ethoxy, propoxy, isopropoxy, butoxy, pentoxy, hexyloxy, heptyloxy, and octyloxy, and the like.

The term "substituted methylene" refers to ethylidene, dimethylmethylene, methylethylmethylene, diethylmethylene, or the like.

The term "halogen" refers to chlorine, bromine, iodine and fluorine.

The term "alkali metal" refers to lithium, potassium or sodium.

The preferred examples of R are phenyl, o-tolyl, m-tolyl, p-tolyl, 4-ethylphenyl, 4-pentylphenyl, 4-hydroxyphenyl, 4-methoxyphenyl, 4-fluorophenyl, 4-bromophenyl, and 4-chlorophenyl. The preferred examples of Y are methylene, dimethylmethylene, ethylene, vinylene and oxygen.

Particularly preferred sulfonamide derivatives of Formula (I) are the compounds (I) wherein R is phenyl, p-tolyl, 4-hydroxyphenyl or 4-bromophenyl; Y is methylene or oxygen; and m is 1, n is 0, or m is 0, n is 1.

The trans/cis sulfonamide derivatives (I)', the starting material of the present invention, can be prepared by cleaving the corresponding compounds having an unsaturated alkyl such as an allyl group at the 2-position in the manner as disclosed in the afore-mentioned Japanese Patent Publication.

Anionoid or carbonyl reagents which can be used as a resolving agent in the method of the present invention are selected from those capable of forming a water-soluble adduct with a formyl group of the compound (I). Typical anionoid reagents are metal-hydrogen sulfites, such as sodium hydrogen sulfite and sodium cyanide. Typical soluble carbonyl reagents are Girard reagents T and P. Anionoid reagents, especially sodium hydrogen sulfite, are preferred in the process of the present invention.

According to the present invention, the starting compound (I)' is reacted with a selected anionid or carbonyl reagent using known reaction conditions in the art. The compound (I)' may be reacted with an anionoid reagent in a molecular ratio of 1:1-1:10 in a solvent containing water and a relatively inert organic solvent, such as dichloromethane, in which aqueous layer has been adjusted to pH 3-7, preferably about pH 4. Alternatively, the solvent used for the proceeding ozonolysis reaction can be used as such to make the reaction more convenient. Temperature in the range of about 0° C.–40° C. may be employed with a preferred temperature being about 20° C.±5° C. Under these conditions, the trans isomer of the compound (I)' forms a water-soluble adduct with the selected resolving agent, while the cis isomer remains unchanged. The organic layer containing the latter is separated from the aqueous layer and the organic layer is extracted with water again. The aqueous extracts are combined, and the free aldehyde (I) is recovered from the combined aqueous phase by conventional methods. For example, the aqueous phase containing the adduct is treated with a base to release the free aldehyde, which is then extracted with a water-immiscible solvent such as dichloromethane, in which the trans isomer is soluble.

The process of the invention provides a high degree of separation of the trans isomer (I) from not only the cis-isomer but also other non-aldehydes, as reflected by its purity. Thus, the trans isomer (I) which has been obtained by evaporating the solvent to dryness has more than about 99% purity.

The process of the present invention as detailed in the above is applicable to any compounds described in the afore-mentioned Japanese Patent Publication, provided that their trans isomers can form a water-soluble adduct with an anionoid reagent or a carbonyl reagent, while cis isomers fail to form an adduct under the reaction condition described above.

The adducts of the trans isomer with an anionoid reagent are novel, and can be shown by the following Formula (III):

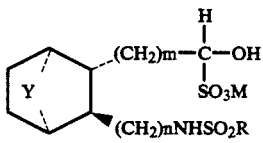

where R, Y, m and n are as defined above, and M is an alkali metal. The adducts can be easily decomposed to give the desired free aldehyde of Formula (I) by addition of a base such as sodium hydroxide.

As previously mentioned, sodium hydrogen sulfite is a preferred anionoid reagent. The metal hydrogen sulfite adduct of 2,3-trans-1,4-bridged cyclohexane sulfonamide of Formula (III) is especially useful among others as an intermediate for the mass production of the final trans carboxylic acid derivative which exhibits a potent antagonistic action against $TXA_2$. Thus, as a further aspect of the invention, there are provided the novel compounds of Formula (III), inter alia, the compound (III) wherein M is sodium.

The following example is set forth to further describe the invention but in no way meant to be construed as limiting the scope thereof.

EXAMPLE 1

(2 S*)-2-Exo-3-endo-2-formylmethyl-3-phenylsulfonylamino-bicyclo[2,2,1]heptane

A. Reaction

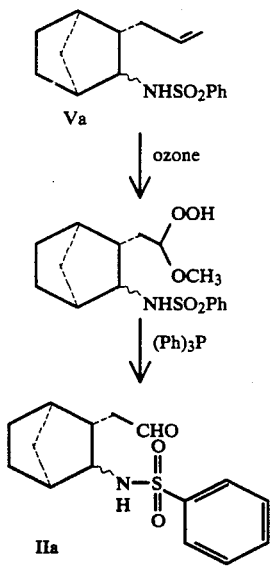

8.0 g (27 mmol) of sulfonamide (Va) is dissolved in a mixture of 6 ml of methanol and 100 ml of dichrolomethane, and cooled to −65° C. To the solution was introduced 1.18 equivalents of theoretically necessary amounts of ozone at −60° C. over 1 hr. After removal of the excess of ozone from the reaction mixture by introducing $N_2$ gas at the same temperature for 10 minutes, 8.6 g (1.2 eq.) of $(Ph)_3P$ in 12 ml of dichloromethane is added dropwise to the mixture at −60° C. over 10 minutes. The resulting mixture is gradually warmed up to 0° C. over 15 minutes and allowed to stand for 3 hr at the same temperature. The reaction mixture is poured into 40 ml of a 1% aqueous sodium thiosulfate solution.

The organic layer is separated and the aqueous layer is extracted with dichloromethane. After washing 2 times with water, the dichloromethane layers containing the trans/cis mixture of compound (IIa) are combined.

B. Separation

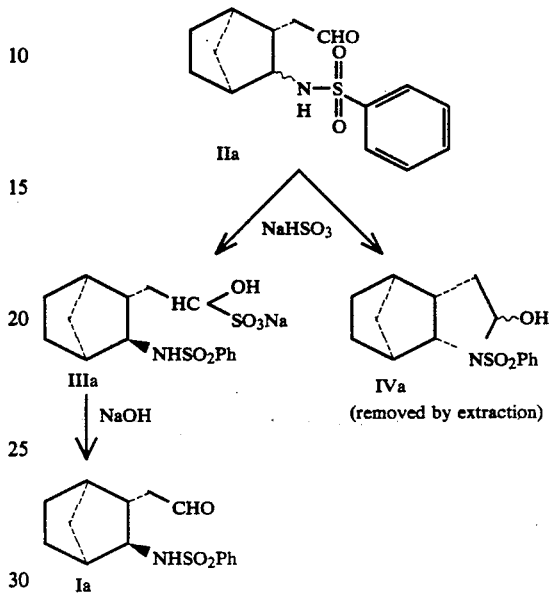

To the dichloromethane solution containing compound (IIa) is added 60 ml (3 eq.) of a 17.5% aqueous solution of sodium hydrogen sulfite and the mixture is stirred at 20° C. for 30 minutes. The mixture is separated and the organic solution is extracted with water, and the water extracts containing (IIIa) are washed with dichloromethane and combined (dichloromethane layers containing the compound (IVa) are discarded). The aqueous solution is mixed with 70 ml of dichloromethane and cooled to 5° C. To the cooled solution is added dropwise over about 1 hr 17 ml (3 eq.) of a 24% NaOH solution previously cooled to 10° C., while the reaction temperature being maintained at 5° C. (pH ÷ 11). The mixture is separated and the aqueous layer is extracted with dichloromethane. The organic solutions are washed with water (×3), combined, and concentrated to dryness under reduced pressure to obtain 9 g of the crude titled trans sulfonamide. Recrystallization from ether-petroleum ether gives compound (Ia). Yield=6.84 g (85%). M.p.=83.8°-84.8° C.

In the same manner as above, optically active (Ia) is obtained from optically active (Va). M.p.=100°-103° C.

$[\alpha]_D = +36.5 \pm 0.8°$ ($CHCl_3$, C=0.994%, 25.5° C.)
Physico-chemical properties of intermediates (IIIa) and (IVa) are shown below:

(IIIa);

IRγmax (Nujol): 3100-3500 (broad), 1640, 1320, 1150, 1100, 1040, 950, 890 $cm^{-1}$ cis formyl compound (IVa);

NMR ($CDCl_3$) δppm: 0.9-1.3 (6 H, m), 1.52 (1 H, m), 1.8-2.0 (1 H, m), 2.06 (1 H, dd, J=9.1, 13.5 Hz), 2.3-2.4 (1 H, m), 2.4-2.5 (1 H, m), 3.26 (1 H, dd, J=2, 2.6 Hz), 3.65 (1 H, dd, J=1.2, 7.6 Hz), 5.47 (1 H, dd, J=2.6, 5 Hz), 7.5-7.7 (3 H, m), 7.8-7.95 (2 H, m).

What we claim is:

1. Alkali metal hydrogen sulfite salt of 2,3-trans-1,4-bridged cyclohexane sulfonamide derivative of Formula (III):

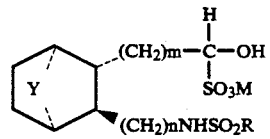

where R is phenyl or phenyl substituted with hydroxy, lower alkoxy, halogen or lower alkyl; Y is unsubstituted or substituted methylene, ethylene, vinylene or oxygen; m is 0 or 1; n is 0, 1 or 2 with the proviso that when m is 0, n is not 0, and when m is 1, n is not 2; and M is an alkali metal.

2. The salt of claim 1 wherein M is sodium.